United States Patent [19]

Haberkorn et al.

[11] 3,933,814
[45] Jan. 20, 1976

[54] 1-(4-PHENOXYPHENYL)-1,3,5-TRIAZINES

[75] Inventors: Axel Haberkorn, Wuppertal; Heinrich Kölling, Haan, Rhineland; Eckart Kranz, Wuppertal; Jürgen Schramm, Dormagen, all of Germany

[73] Assignee: Bayer Aktiengesellschaft, Germany

[22] Filed: Sept. 17, 1973

[21] Appl. No.: 397,812

[30] Foreign Application Priority Data
Sept. 20, 1972 Germany............... 2246109

[52] U.S. Cl..... 260/248 NS; 424/249; 260/242 LM; 260/247.5 C; 260/247.2 R; 260/247.2 A; 260/247.2 B
[51] Int. Cl.²......................... C07D 251/26
[58] Field of Search.............. 260/248 NS, 247.2 A, 260/247.2 R, 247.2 B, 247.1 M, 247.5 C

[56] References Cited
UNITED STATES PATENTS
3,669,961  6/1972  Gilles ................................ 260/248
FOREIGN PATENTS OR APPLICATIONS
250,977  12/1966  Austria Primary Examiner—John M. Ford

[57] ABSTRACT

1-(4-Phenoxyphenyl)-1,3,5-triazines of the formula:

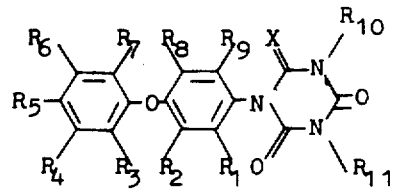

or pharmaceutically acceptable nontoxic salts thereof are produced by reacting a urea or thiourea derivative of the formula:

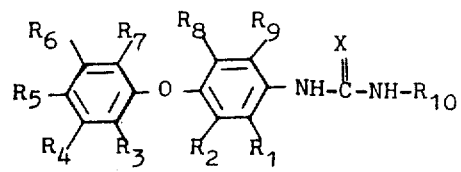

with a carbonylisocyanate of the formula:

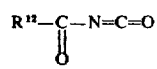

to produce a 1-(4-phenoxyphenyl)-1,3,5-triazine as above defined wherein $R^{11}$ is hydrogen, and when a 1-(4-phenoxyphenyl)-1,3,5-triazine as above defined wherein $R^{11}$ is alkyl is desired, reacting the triazine wherein $R^{11}$ is hydrogen with a compound of the formula $(alk)_n Y$.

The above defined triazines and their salts are useful as agents against protozoan infections and are particularly useful against coccidiosis.

22 Claims, No Drawings

1-(4-PHENOXYPHENYL)-1,3,5-TRIAZINES

The present invention is concerned with 1-(4-phenoxyphenyl)-1,3,5-triazines, pharmaceutically acceptable nontoxic salts thereof, a process for their production, and pharmaceutical and veterinary compositions useful for the treatment of protozoan infections and particularly useful for the treatment of coccidiosis infections, and to methods of treating protozoan infections in poultry and mammals.

It is known in the art that 2-phenyl-(2-benzyl)-1,2,4-triazine-3,5(2H,4H)-diones exhibit coccidiostatic activity against poultry coccidiosis (Belgian Pat. No. 740,403, Belgian Pat. No. 773,583).

More particularly, the present invention is concerned with 1-(4-phenoxy-phenyl)-1,3,5-triazines of the formula:

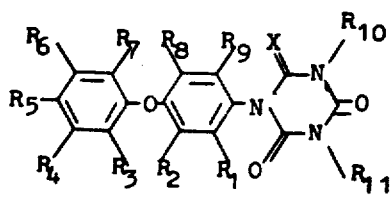

or a pharmaceutically acceptable nontoxic salt thereof wherein $R^1$, $R^2$, $R^3$, $R^4$, $R^5$, $R^6$, $R^7$, $R^8$ and $R^9$ are the same or different and are each hydrogen, straight or branched chain alkyl especially lower alkyl, haloalkyl especially trifluoromethyl, halogen especially chlorine or bromine, nitro, cyano, amino, acylamino especially lower acylamino, alkoxycarbonylamino especially lower alkoxycarbonylamino, carboxyl, alkoxycarbonyl especially lower alkoxycarbonyl, aminocarbonyl, alkylcarbonyl especially lower alkylcarbonyl, alkylsulphonyl especially lower alkylsulphonyl or aminosulphonyl;

$R^{10}$ is hydrogen, straight or branched chain alkyl especially lower alkyl, cycloalkyl especially cyclohexyl, haloalkyl especially of 1 or 2 carbon atoms in the alkyl moiety and 1 halo moiety, alkoxyalkyl especially lower alkoxy lower alkyl, alkenyl especially lower alkenyl, alkinyl especially lower alkinyl, alkoxycarbonyl especially lower alkoxycarbonyl, thioalkylcarbonyl especially thiolower alkylcarbonyl, alkoxy especially lower alkoxy, dialkylamino especially dilower alkylamino, a polymethyleneimino moiety, a polymethyleneimino moiety containing a heteroatom especially piperidyl and morpholino, benzyl unsubstituted or substituted by one or more substituents especially benzyl unsubstituted or substituted by one or two chlorine or bromine moieties, or aryl unsubstituted or substituted by one or more substituents especially phenyl or phenyl substituted by chlorine or bromine;

$R^{11}$ is hydrogen or alkyl especially lower alkyl and X is oxygen or sulfur.

The triazines and their salts above defined are particularly useful because of their activity against coccidiosis both in poultry and in mammals.

The triazines and their salts of the present invention may be produced by reacting a urea or thiourea of the formula:

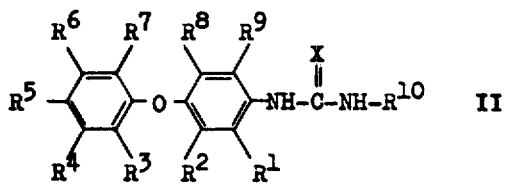

wherein $R^1$, $R^2$, $R^3$, $R^4$, $R^5$, $R^6$, $R^7$, $R^8$, $R^9$, $R^{10}$ and X are as above defined with a carbonylisocyanate of the formula:

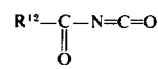

wherein $R^{12}$ is halogen especially chlorine or bromine, alkoxy especially lower alkoxy, or aryloxy especially phenoxy, to produce a triazine of the formula:

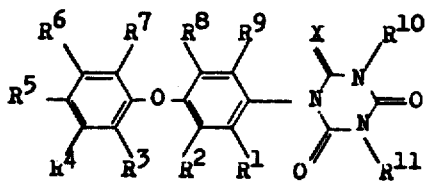

wherein $R^1$, $R^2$, $R^3$, $R^4$, $R^5$, $R^6$, $R^7$, $R^8$, $R^9$, $R^{10}$, and X are as above defined; and $R^{11}$ is hydrogen, and when a triazine wherein $R^{11}$ is alkyl especially lower alkyl is desired, reacting said triazine wherein $R^{11}$ is hydrogen with a compound of the formula:

 IV wherein alk is alkyl, especially lower alkyl;

$n$ is 1, 2 or 3; and

Y is an anion forming moiety which is eliminated together with the acid hydrogen of the imino group of the triazine in which $R^{11}$ is hydrogen as $H_nY$.

The triazines of the present invention and their salts may be interconverted according to techniques per se known.

It was particularly surprising that the 1-(4-phenoxyphenyl)-1,3,5-triazines and the salts thereof defined above are active against both coccidiosis in poultry and in mammals. This double action was not exhibited by compounds known in the art and it was therefore particularly surprising that the present compounds would exhibit activity against coccidiosis both of poultry and of mammals.

If N-[4-(4'-nitrophenoxy)-phenyl]-N'-methylurea (formula II) and chlorocarbonylisocyanate (formula III) are used as starting compounds, and methyl chloride as the alkylating agent (formula IV), the course of the reaction can be represented by the following equation:

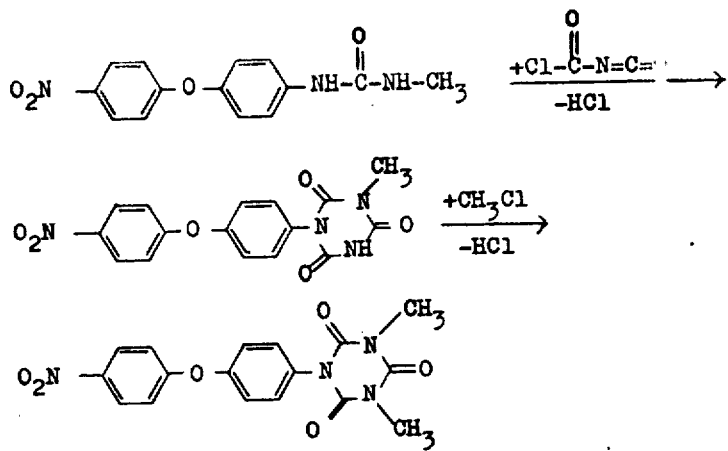

According to one embodiment of the present invention, $R^1$, $R^2$, $R^3$, $R^4$, $R^5$, $R^6$, $R^7$, $R^8$ and $R^9$ are the same or different and are each hydrogen, straight chain alkyl of one to four carbon atoms, trifluoromethyl, chlorine, bromine, nitro, cyano, amino, acylamino of one to four carbon atoms in the acyl moiety, alkoxycarbonylamino of one to four carbon atoms in the alkoxy moiety, carboxyl, alkoxycarbonyl of one to four carbon atoms in the alkoxy moiety, aminocarbonyl, alkylcarbonyl of one to four carbon atoms in the alkyl moiety, alkylsulphonyl of one to four carbon atoms in the alkyl moiety, or aminosulphonyl;

$R^{10}$ is hydrogen, straight chain alkyl of one to 12 carbon atoms, branched chain alkyl of three to five carbon atoms, an ω-chloroalkyl moiety of one to six carbon atoms, an ω-methoxyalkyl moiety of two to five carbon atoms, alkenyl of two to four carbon atoms, alkoxycarbonyl of one to four carbon atoms in the alkoxy moiety, thioalkylcarbonyl of one to four carbon atoms in the alkyl moiety, dialkylamino wherein the alkyl moieties are the same and each contains one to four carbon atoms, a polymethyleneimino moiety particularly piperidyl or morpholino, phenyl or phenyl substituted by halogen especially chlorine or bromine; and $R^{11}$ is hydrogen or alkyl of one to four carbon atoms.
$R^{12}$ is preferably chlorine, methoxy or phenoxy;
Alk is preferably alkyl or one to four carbon atoms; and
Y is preferably halogen especially chlorine, bromine or iodine, or a —$SO_4$ moiety.

According to another embodiment of the present invention, $R^1$, $R^2$, $R^3$, $R^4$, $R^5$, $R^6$, $R^7$, $R^8$ and $R^9$ are the same or different and each are hydrogen, chlorine, methyl, nitro, cyano, amino, trifluoromethyl, methylcarbonylamino, carboxyl, acetyl, carbethoxy, carbethoxyamino, ethylsulphonyl, aminocarbonyl or aminosulphonyl;

$R^{10}$ is hydrogen, straight or branched chain alkyl of one to 10 carbon atoms, allyl, chloroethyl, alkoxycarbonyl of one or two carbon atoms in the alkoxy moiety, thioalkylcarbonyl of one to four carbon atoms in the alkyl moiety, methoxy, methoxyalkyl of one to three carbon atoms, dimethylamino, phenyl, chlorophenyl, dichlorotolyl, piperidyl or morpholino;

$R^{11}$ is hydrogen; and
X is oxygen or sulphur.

According to a further embodiment of the present invention, $R^1$ is hydrogen, chlorine or methyl;
$R^2$ is hydrogen, chlorine, methyl, trifluoromethyl or nitro;
$R^3$ is hydrogen, chlorine, nitro, amino, cyano, methyl or trifluoromethyl;
$R^4$ is hydrogen, chlorine, methyl, cyano or trifluoromethyl;
$R^5$ is hydrogen, chlorine, methyl, nitro, amino, methylcarbonylamino, carboxyl, carbethoxy, cyano, trifluoromethyl, acetyl, carbethoxyamino, ethylsulphonyl, aminocarbonyl or aminosulphonyl;
$R^6$ is hydrogen, chlorine, methyl or nitro;
$R^7$ is hydrogen, chlorine, methyl, nitro or trifluoromethyl;
$R^8$ is hydrogen, chlorine or methyl;
$R^9$ is hydrogen, chlorine or methyl;
$R^{10}$ is hydrogen, methyl, ethyl, n-propyl, i-propyl, n-butyl, t-butyl, hexyl, decyl, chloroethyl, allyl, methoxy, methoxypropyl, methoxycarbonyl, carbethoxy, thiobutylcarbonyl, phenyl, chlorophenyl, dichlorotolyl, pyridyl or morpholino;
$R^{11}$ is hydrogen; and
X is oxygen or sulfur.

The 4-phenoxyphenyl ureas or thioureas of formula II used as starting compounds for producing the triazine to the present invention are generally not known but such compounds can be produced either:

a. by reacting a substituted 4-aminodiphenyl ether with the appropriate substituted isocyanate or isothiocyanate in an inert organic solvent, if necessary in the presence of a tertiary base such as triethylamine or pyridine, at temperatures between 0°C and 100°C; or b. conversely, by allowing a substituted amine to react with the appropriately substituted 4-isocyanato-diphenyl ether or 4-isothiocyanato-diphenyl ether under the same conditions.

The reaction products crystallize out on cooling the solution, if the amount of solvent has been appropriately chosen.

Literature for the reciprocal preparation of ureas from amines and isocyanates: "Methoden der Org. Chemie" (Houben-Weyl) IV Edition, Vol. VIII, p.157-158.

Representative ureas of the formula II which can be used in the process of the present invention include:
4-(4'-nitro-phenoxy)-phenyl-urea, mp 197°C, 3-chloro-4-(2',4',5'-trichloro-phenoxy)-phenyl-urea mp 232°C,
N-[4-(phenoxy)-phenyl]-N'-methyl-urea, mp 168°C,
N-[4-(4'-methyl-phenoxy)-phenyl]-N'-methyl-urea, mp 151°C,
N-[3-chloro-4-(2',4'-dimethyl-phenoxy)-phenyl]-N'-methyl-urea, mp 125°C,
N-[4-(3',5'-dimethyl-4-chloro-phenoxy)-phenyl]-N'-methyl-urea, mp 194°C,
N-[3,5-dimethyl-4-(2',4'-dichloro-phenoxy)-phenyl]-N'-methyl-urea,
N-[3,5-dimethyl-4-(4'-chloro-phenoxy)-phenyl]-N'-methyl-urea, mp 160°C,
N-[4-(4'-nitro-phenoxy)-phenyl]-N'-methyl-urea
N-[4-(3'-nitro-phenoxy)-phenyl]-N'-methyl-urea,
N-[4-(2',4'-dinitro-phenoxy)-phenyl]-N'-methyl-urea, mp 235°C,
N-[4-(3'-chloro-4'-nitro-phenoxy)-phenyl]-N'-methyl-urea, mp 218°C,
N-[4-(2',5'-dichloro-4'-nitro-phenoxy)-phenyl]-N'-methyl-urea, mp 218°C,
N-[2-chloro-4-(3'-chloro-4'-nitro-phenoxy)-phenyl]-N'-methyl urea, mp 191°C,
N-[3-chloro-4-(2'-chloro-4'-nitro-phenoxy)-phenyl]-N'-methyl-urea, mp 196°C,
N-[4-(2'-nitro-4'-chloro-phenoxy)-phenyl]-N'-methyl-urea, mp 214°C,
N-[4-(2'-nitro-6'-chloro-phenoxy)-phenyl]-N'-methyl-urea, mp 218°C,
N-[4-(2'-methyl-4'-nitro-phenoxy)-phenyl]-N'-methyl-urea, mp 217°C,
N-[2-chloro-4-(2'-chloro-4'-nitro-phenoxy)-phenyl]-N'-methyl-urea, mp 192°C,
N-[3,5-dichloro-4-(2'-chloro-4'-nitro-phenoxy)-phenyl]-N'-methyl-urea, mp 235°C,
N-[3,5-dichloro-4-(2',6'-dimethyl-4'-nitro-phenoxy)-phenyl]-N'-methyl-urea,
N-[3,5-dichloro-4-(4'-nitro-phenoxy)-phenyl]-N'-methyl-urea, mp 230°C,
N-[3,5-dichloro-4-(2'-methyl-4'-nitro-phenoxy)-phenyl]-N'-methyl-urea,
N-[3,5-dimethyl-4-(4'-nitro-phenoxy)-phenyl]-N'-methyl-urea, mp 214°C,
N-[3,5-dimethyl-4-(2'-chloro-4'-nitro-phenoxy)-phenyl]-N'-methyl-urea, mp 250°C,
N-[3,5-dimethyl-4-(2',6'-dichloro-4'-nitro-phenoxy)-phenyl]-N'-methyl-urea,
N-[4-(4'-amino-phenoxy)-phenyl]-N'-methyl-urea,
N-[4-(2'-amino-phenoxy)-phenyl]-N'-methyl-urea,
N-[2-chloro-4-(2'-chloro-4'-amino-phenoxy)-phenyl]-N'-methyl-urea,
N-[4-(4'-acetylamino-phenoxy)-phenyl]-N'-methyl-urea,
N-[4-(4'-ethoxycarbonylamino-phenoxy)-phenyl]-N'-methyl-urea, mp 164°C,
N-[4-(4'-chloro-phenoxy)-phenyl]-N'-methyl-urea, mp 184°C,
N-[2-chloro-4-phenoxy-phenyl]-N'-methyl-urea,
N-[4-(3'-chloro-phenoxy)-phenyl]-N'-methyl-urea, mp 136°C,
N-[4-(2',4'-dichloro-phenoxy)-phenyl]-N'-methyl-urea mp 191°C,
N-[4-(4'-ethylsulphonyl-phenoxy)-phenyl]-N'-methyl-urea, mp 131°C,
N-[4-(4'-aminosulphonyl-phenoxy)-phenyl]-N'-methyl-urea,
N-[4-(2',4'-dimethyl-phenoxy)-phenyl]-N'-ethyl-urea, mp 162°C,
N-[4-(3',4'-dimethyl-phenoxy)-phenyl]-N'-ethyl-urea, mp 148°C,
N-[2-ethyl-4-(4'-nitro-phenoxy)-phenyl]-N'-ethyl-urea,
N-[2-chloro-4-(4'-nitro-phenoxy)-phenyl]-N'-ethyl-urea, mp 190°C,
N-[2-chloro-4-(4'-amino-phenoxy)-phenyl]-N'-ethyl-urea,
N-[2-methyl-4-(2'-chloro-4'-nitro-phenoxy)-phenyl]-N'-ethyl-urea, mp 206°C,
N-[4-(4'-nitro-phenoxy)-phenyl]-N'-ethyl-urea, mp 200°C,
N-[4-(4'-nitro-phenoxy)-phenyl]-N'-propyl-urea, mp 182°C,
N-[4-(4'-nitro-phenoxy)-phenyl]-N'-isopropyl-urea, mp 202°C,
N-[4-(4'-nitro-phenoxy)-phenyl]-N'-n-butyl-urea, mp 168°C,
N-[4-(4'-nitro-phenoxy)-phenyl]-N'-tert.-butyl-urea, mp 158°C,
N-[4-(2'-chloro-4'-nitro-phenoxy)-phenyl]-N'-n-butyl-urea,
N-[4-(4'-nitro-phenoxy)-phenyl]-N'-decyl-urea, mp 136°C,
N-[4-(4'-nitro-phenoxy)-phenyl]-N'-chloromethyl-urea,
N-[4-(4'-nitro-phenoxy)-phenyl]-N'-β-chloroethyl-urea, mp 171°C,
N-[4-(4'-nitro-phenoxy)-phenyl]-N'-allyl-urea, mp 180°C,
N-[4-(4'-nitro-phenoxy)-phenyl]-N'-cyclohexyl-urea, mp 200°C,
N-[4-(4'-nitro-phenoxy)-phenyl]-N'-phenyl-urea, mp 208°C,
N-[4-(4'-nitro-phenoxy)-phenyl]-N'-4-chlorophenyl-urea, mp 235°C,
N-[4-(4'-nitro-phenoxy)-phenyl]-N'-ethoxycarbonyl-urea, mp 175°C,
N-[4-(4'-nitro-phenoxy)-phenyl]-N'-methoxycarbonyl-urea,
N-[4-(4'-nitro-phenoxy)-phenyl]-N'-n-butylmercaptocarbonyl-urea, mp 133°C,
N-[4-(4'-nitro-phenoxy)-phenyl]-N'-amino-urea, mp 160°C,
N-[4-(4'-nitro-phenoxy-phenyl]-N'-dimethyl-amino-urea, mp 138°C,
N-[4-(4'-nitro-phenoxy)-phenyl]-N'-piperidino-urea, mp 210°C,
N-[4-(4'-nitro-phenoxy)-phenyl]-N'-morpholino-urea, mp 169°C,
N-[4-(4'-nitro-phenoxy)-phenyl]-N'-methoxymethyl-urea, mp 177°C,
N-[4-(4'-nitro-phenoxy)-phenyl]-N'-hydroxy-urea,
N-[4-(4'-nitro-phenoxy)-phenyl]-N'-methoxy-urea, mp 173°C,
N-[3-chloro-4-(2',4',5'-trichloro-phenoxy)-phenyl]-N'-3,4,-dichlorobenzyl-urea, mp 224°C,
N-[4-(4'-chloro-phenoxy)-phenyl]-N'-γ-methoxypropyl-urea, mp 125°C,
N-[4-(4'-chloro-phenoxy)-phenyl]-N'-morpholino-urea, mp 195°C,
N-[4-(4'-chloro-phenoxy)-phenyl]-N'-allyl urea, mp 163°C,
N-[3-chloro-4-(2',4'-dichloro-phenoxy)-phenyl]-N'-methoxycarbonyl-urea, mp 153°C,
N-[3-chloro-4-(3',4',6'-trichloro-phenoxy)-phenyl]-N'-methoxy-carbonyl-urea, N-[3,5-dichloro-4-(2'-chloro-4'-nitro-phenoxy)-phenyl]-N'-ethyl-urea, mp 213°C,
N-[3,5-dichloro-4-(2'-chloro-4'-nitro-phenoxy)-phenyl]-N'-propyl-urea, mp 212°C,
N-[3,5-dichloro-4-(2'-chloro-4'-nitro-phenoxy)-phenyl]-N'-isopropyl-urea, mp 231°C,
N-[3,5-dichloro-4-(2'-chloro-4'-nitro-phenoxy)-phenyl]-N'-allyl-urea, mp 190°C,
N-[3,5-dichloro-4-(2'-chloro-4'-nitro-phenoxy)-phenyl]-N'-butyl-urea, mp 178°C,
N-4-phenoxy-phenyl-N'-methyl-thiourea, mp 121°C,
N-[4-(4'-nitro-phenoxy)-phenyl]-N'-methyl-thiourea, mp 206°C,
N-3-chloro-4-phenoxy-phenyl-N'-methyl-thiourea, mp 183°C,
N-[4-(4'-chloro-phenoxy)-phenyl]-N'-methyl-thiourea, mp 171°C,
N-[3-chloro-4-(4'-chloro-phenoxy)-phenyl]-N'-methyl-thiourea, mp 143°C,
N-[4-(2',4'-dichloro-phenoxy)-phenyl]-N'-methyl-thiourea, mp 123°C,
N-[3-chloro-4-(2',4'-dichloro-phenoxy)-phenyl]-N'-methyl-thiourea, mp 124°C,
N-[3-chloro-4-(2',4',5'-trichloro-phenoxy)-phenyl]-N'-methyl-thiourea, mp 136°C,
N-[3,5-dichloro-4-(2'-chloro-4'-nitro-phenoxy)-phenyl]-N'-methyl-urea, mp 235°C,
N-[3,5-dichloro-4-(2'-chloro-4'-nitro-phenoxy)-phenyl]-N'-propyl-urea,
N-[3-methyl-4-(4'-chloro-phenoxy)-phenyl]-N'-methyl-urea, mp 148°C,
N-[3-methyl-4-(4'-chloro-phenoxy)-phenyl]-N'-propyl-urea,
N-[3-methyl-4-(2',-dichloro-phenoxy)-phenyl]-N'-methyl-urea, mp 183°C,
N-[3-methyl-4-(2',-dichloro-phenoxy)-phenyl]-N'-propyl-urea,
N-[3-chloro-4-(2'-methyl-4'-chloro-phenoxy)-phenyl]-N'-methyl-urea, mp 184°C,
N-[3-chloro-4-(2',4'-dichloro-phenoxy)-phenyl]-N'-propyl-urea,
N-[3-chloro-4-(2'-methyl-4'-chloro-phenoxy)-phenyl]-N'-propyl-urea,
N-[3-methyl-5-chloro-4-(4'-chloro-phenoxy)-phenyl]-N'-methyl-urea, mp 202°C,
N-[3-methyl-5-chloro-4-(4'-chloro-phenoxy)-phenyl]-N'-propyl-urea,
N-[3-nitro-4-(4'-chloro-phenoxy)-phenyl]-N'-methyl-urea, and
N-[3-nitro-4-(4'-chloro-phenoxy)-phenyl]-N'-propyl-urea.

Any inert organic solvent can be used as a diluent both for the reaction of the ureas or thioureas of the formula II with the carbonylisocyanate of the formula III and for the reaction of the 1,3,5-triazines wherein R$^{11}$ is hydrogen with a compound of the formula IV. Preferred solvents for this purpose include aromatic hydrocarbons such as benzene, toluene and xylene, halogenated aromatic hydrocarbons such as chlorobenzene and dichlorobenzene, and ethers, such as tetrahydrofurane and dioxane.

When R$^{12}$ is halogen, hydrogen halide R$^{12}$ produced in the reaction is evolved in the form of a gas or can be bound by organic or inorganic acid acceptors. Preferred acid acceptors include tertiary organic bases such as triethylamine and pyridine, as well as inorganic bases such as alkali metal carbonates or alkaline earth metal carbonates.

The reaction temperatures for the above described processes can be varied within a substantial range. In general, the reactions are carried out at between 0°C and 150°C, and preferably at between 20°C and 100°C.

The above described processes can be carried out either under normal pressure or elevated pressure. Generally, atmospheric pressure is used.

According to the process of the present invention, the starting compounds are generally reacted in molar amounts.

The following triazines are respresentative of those of the present invention:

1-[3,5-dimethyl-4-(2',4'-dichloro-phenoxy)-phenyl]-3-propyl-1,3,5-triazine-2,4,6(1H,3H,5H)-trione,
1-[3,5-dichloro-4-(4'-nitro-2'-methyl-phenoxy)-phenyl]-3-methyl-1,3,5-triazine-2,4,6(1H,3H,5H)-trione,
1-[3,5-dichloro-4-(4'-nitro-2'-methyl-phenoxy)-phenyl]-3-propyl-1,3,5-triazine-2,4,6(1H,3H,5H)-trione,
1-[3,5-dichloro-4-(4'-nitro-2',6'-dimethyl-phenoxy)-phenyl]-3-methyl-1,3,5-triazine-2,4,6(1H,3H,5H)-trione,
1-[3,5-dichloro-4-(4'-nitro-2',6'-dimethyl-phenoxy)-phenyl]-3-propyl-1,3,5-triazine-2,4,6(1H,3H,5H)-trione,
1-[3,5-dimethyl-4-(4'-nitro-2',6'-dichloro-phenoxy)-phenyl]-3-methyl-1,3,5-triazine-2,4,6(1H,3H,5H)-trione,
1-[3,5-dimethyl-4-(4'-nitro-2',6'-dichloro-phenoxy)-phenyl]-3-propyl-1,3,5-triazone-2,4,6(1H,3H,5H)-trione,
1-[3,5-dichloro-4-(4'-trifluoromethyl-phenoxy)-phenyl]-3-methyl-1,3,5-triazine-2,4,6(1H,3H,5H)-trione,
1-[3,5-dichloro-4-(4'-trifluoromethyl-phenoxy)-phenyl]-3-propyl-1,3,5-triazine-2,4,6(1H,3H,5H)-trione,
1-[4-(4'-aminocarbonyl-phenoxy)-phenyl]-3-propyl-1,3,5-triazine-2,4,6(1H,3H,5H)-trione,
1-[4-(4'-aminosulphonyl-phenoxy)-phenyl]-3-methyl-1,3,5-triazine-2,4,6(1H,3H,5H)-trione,
1-[4-(4'-aminosulphonyl-phenoxy)-phenyl]-3-propyl-1,3,5-triazine-2,4,6(1H,3H,5H)-trione,
1-[3-methyl-4-(4'-chloro-phenoxy)-phenyl]-3-propyl-1,3,5-triazine-2,4,6(1H,3H,5H)-trione,
1-[3-methyl-4-(2',4'-dichloro-phenoxy)-phenyl]-3-propyl-1,3,5-triazine-2,4,6(1H,3H,5H)-trione,
1-[3-chloro-4-(2',4'-dichloro-phenoxy)-phenyl]-3-propyl-1,3,5-triazine-2,4,6(1H,3H,5H)-trione,
1-[3-chloro-4-(2'-methyl-4'-chloro-phenoxy)-phenyl]-3-propyl-1,3,5-triazine-2,4,6(1H,3H,5H-trione,
1-[3-methyl-5-chloro-4-(4'-chloro-phenoxy)-phenyl]-3-propyl-1,3,5-triazine-2,4,6(1H,3H,5H)-trione,
1-[3-nitro-4-(4'-chloro-phenoxy)-phenyl]-3-methyl-1,3,5-triazine-2,4,6(1H,3H,5H)-trione, and
1-[3-nitro-4-(4'-chloro-phenoxy)-phenyl]-3-propyl-1,3,5-triazone-2,4,6(1H,'H,5H)-trione.

The salts of the triazines of the present invention are preferably the pharmaceutically acceptable nontoxic salts.

The triazines of the present invention exhibit strong coccidiocidal effects. They are highly active against the varieties of coccidia of poultry such as, for example *Eimeria tenella* (chicken appendix coccidiosis), *E. acer-*

*vulina, E. brunetti, E. maxima, E. mitis, E. mivati, E. necatrix* and *E. praecox* (chicken small intestine coccidiosis). The new compounds can also be employed for the prophylaxis and treatment of coccidiosis infections of other types of domestic poultry. The new active compounds are additionally also distinguished by a very strong activity in coccidial infections of mammals such as, for example, of rabbits (*E. stiedae*/coccidiosis of the liver, *E. magna, E. media, E. irresidua* and *E. perforans*/intestinal coccidiosis) of sheep, cattle and other domestic animals including dogs and cats as well as laboratory animals such as white mice (*E. falciformis*) and rats.

Coccidial infections can lead to severe losses in the case of domestic animals and thus represent a real problem in the raising of poultry and mammals such as oxen, sheep, rabbits and dogs. The action of the previously known agents against coccidiosis is in most cases restricted to a few varieties of poultry. The treatment and prophylaxis of coccidiosis of mammals has hitherto represented an as yet largely unsolved problem.

Furthermore, a very stong activity against toxoplasmosis has been found. In this infection, the triazines of the present invention and their salts can be employed both for the treatment of the cats which excrete the infectious stages (oocysts) and for the treatment of the human patient.

Furthermore, the triazines of the present invention and their salts are active against malarial parasites (for example *Plasmodium berghei*/mice) and against *Ascaridia* infections of poultry (for example *Ascaridia galli*/chickens).

According to the present invention, a pharmaceutical or veterinary composition is produced which comprises an antiprotozoan, or coccidiostatic or coccidiocidal amount of a triazine of the present invention or salt thereof in combination with a pharmaceutically acceptable nontoxic inert diluent or carrier.

The triazines of the present invention can also be used for the production of fodder premixes and medicated animal fodders.

While the triazines of the present invention and their salts are usually most appropriately administered in or with the feed or in the drinking water, the triazines and their salts can also be administered to individual animals in the form of tablets, medicinal draughts, capsules or the like, or by injection. These last-mentioned modes of administration are of course less suitable for the treatment of large groups of animals than for the treatment of a limited number of animals; they are, however, very suitable for administration to a small number of animals or to individual animals.

For the treatment of large numbers of animals, therefore, a medicated animal fodder may be produced which comprises at least one nutritious ingestible material and a triazine of the present invention or salt thereof. Preferably, the medicated fodder is prepared by thoroughly mixing 50 to 5,000, preferably 80 to 250, ppm of triazine or salt thereof with a nutritionally balanced animal feed, for example with the chick feed described below.

If a concentrate or a premix is to be prepared, which is finally to be diluted, in the feed, to the abovementioned values, 1 to 30%, preferably 10 to 20 per cent by weight, of active compound are generally mixed with an edible organic or inorganic material, for example maize meal or maize and soya bean meal, or mineral salts which contain a small amount of an edible dust-suppressing oil, for example maize oil or soya bean oil. The premix thus obtained can then be added to the complete poultry feed before administration.

The following medicated fodder is exemplary of compositions useful for poultry feed:

52.000% of shredded cereal feed
17.990% of shredded soya
5.000% of maize gluten feed
5.000% of wheat wholemeal
3.000% of fishmeal
3.000% of tapioca meal
3.000% of green lucerne grass meal
2.000% of comminuted wheat germs
2.000% of soya oil
1.600% of bone meal
1.500% of whey powder
1.400% of calcium carbonate for feeds
1.000% of calcium phosphate for feeds
1.000% of molasses
0.500% of brewers yeast
0.010% of 1-[3,5-dichloro-4-(2'-chloro-4'-nitrophenoxy)-phenyl]-3-methyl-1,3,5-triazine-2,4,6(1H,3H,5H)-trione 100.000%

The medicated feed is suitable both for curative and for prophylactic use.

For treating individual poultry or mammals, the pharmaceutical or veterinary compositions of the present invention may be administered in unit dosage form.

The pharmaceutical compositions of the present invention contain a major or minor amount e.g. 99.5% to 0.1%, preferably 90% to 0.5% of at least one 1,3,5-triazine as above defined in combination with a pharmaceutically acceptable nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 5 to 250, mg/kg of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl, palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is 250 mg to 22,500 mg of active ingredient.

The pharmaceutical and veterinary compositions of the present invention and the medicated animal feeds of the present invention may also contain other pharmaceutically active compounds, especially imidazole-4,5-dicarboxylic acid amide or a sulphonamide as described below.

In the treatment and prophylaxis of poultry coccidiosis and particularly coccidiosis of chickens, ducks, geese and turkeys, it is preferred to mix 50 to 100 ppm, preferably 80 to 100 ppm of triazine of the present invention or salt thereof with the nutritious feed. It is possible to increase these amounts if the toleration is good. The amount may be decreased through combination of the triazines and salts thereof of the present invention with either imidazole-4,5-dicarboxylic acid amide mentioned above or p-aminobenzenesulphonamides of 2-amino-4,6-dimethylpyrimidine, of 2-aminoquinoxaline, of 2-amino-5-methoxy-pyrimidine and of 2-amino-4-methyl-pyrimidine because such compounds augment the activity of the triazines of the present invention.

While the routes of administration of the triazines and salts thereof of the present invention include oral, parenteral (intramuscularly, intraperitoneally and intravenously), rectal and topical application, oral administration by tablet or oral administration by an animal fodder are particularly preferred.

The coccidiocidal activity of compounds representative of those of the present invention is shown by way of example in Table 1. *Eimeria tenella* (chicken appendix coccidiosis) is given as an example of the activity against poultry coccidia, while *Eimeria falciformis* (mice) is taken as an example of a mammal coccidium. The activity against *E. falciformis* (mice) is representative of the activity against other mammal coccidia, as is shown in Table 2.

Table 1

| Compound of Example No. | Activity Against Poultry Coccidiosis and Mammal Coccidiosis | |
|---|---|---|
| | Eimeria tenella/ chicks [ppm] | Eimeria falciformis/ mice [mg/kg] |
| 5 | 100 | 5 |
| 10 | 100 | 2.5 |
| 15 | 100 | 10 |
| 16 | 100 | 5 |
| 26 | 250 | 2.5 |
| 28 | 250 | 0.5 |
| 37 | 50 | 10 |
| 47 | 25 | 0.5 |
| 50 | 100 | 25 |
| 54 | 50 | 5 |
| 56 | 50 | 5 |
| 58 | 250 | 100 |
| 62 | 50 | 25 |
| 63 | 250 | 250 |
| 84 | 100 | 1 |
| 86 | 100 | 2.5 |
| 89 | 100 | 1 |
| 91 | 250 | 5 |

In each case, the fully effective minimum dose is quoted, in ppm as a feed additive in the case of chicks, and in mg/kg of body weight in the case of mice.

Table 2

Comparison of the Activity Against Various Mammal *Coccidia* of the Compound of Example No. 26

| Animal | Variety of *Eimeria* | Start of Treatment | Number of Treatments | Minimum Fully Effective Dose in mg/kg |
|---|---|---|---|---|
| Mice | E. falciformis | 1 day after infection | 6 | 2.5 |
| Rabbits | E. stiedae E. magna | 10 days after infection | 5 | 5 |
| | E. perforans E. media E. irresidua | 10 days after infection | 5 | 1 |
| Sheep | E. ninakohlyakimovi E. faurei E. arloingi | natural infection | 4 | 10 |

If, for example, 11 day old chicks are infected with 30,000 sporulated oocysts of *Eimeria tenella*, the pathogen of appendix coccidiosis, 50 to 70% of the animals die in the case of the untreated controls. The surviving chicks daily excrete 300,000 to 500,000 oocysts per gram (opg) of faeces from the 7th to the 9th day after infection. In the course of the illness, the weight increase is considerably impaired and severe macroscopically recognizable pathological changes occur in the appendices, which lead to severe hemorrhages. In testing the activity against *E. tenella*, the compounds according to the invention were administered with the feed from 3 days before infection to 9 days after infection (end of experiment).

The number of oocysts was determined with the McMaster chamber (see Engelbrecht et al., "Parasitologische Arbeitsmethoden in Medizin und Veterinarmedizin" ("Parasitological Techniques in Medicine and Veterinary Medicine"), page 172, Academie-Verlag Berlin (1965)).

The treatment of the *Eimeria falciformis* infection of mice given as an example of mammal coccidia was carried out on the 1st, 2nd, 3rd, 6th, 7th and 8th day after infection. The infection was produced with 10,000 sporulated oocysts per mouse (weighing 15 g). In the case of the untreated controls, from the 7th day after infection there is massive excretion of oocysts, diarrhea containing blood, and mortality, attributable to the infection, in the case of 30% of the animals.

With the minimum effective dosages indicated in Table 1, the course of the infection was so lastingly influenced, in chicks and in mice, that the infection caused no set-back, or only an insignificant set-back to the animals.

The following non-limitative examples more particularly illustrate the present invention:

EXAMPLE 1

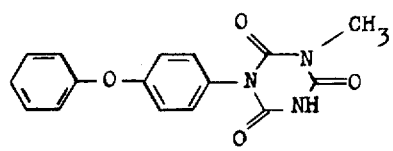

24.2 g (0.1 mol) of N-methyl-N'-(4-phenoxyphenyl)-urea are suspended in 500 ml of absolute toluene and 10.5 g (0.1 mol) of chlorocarbonylisocyanate are added dropwise at room temperature, while stirring. Thereafter the mixture was stirred for a further hour at room temperature and 2 hours at the boil.

After cooling, the 1-(4-phenoxy-phenyl)-3-methyl-1,3,5-triazine-2,4,6(1H,3H,5H)-trione which has separated out is filtered off and stirred with alcohol.

Yield: 80% of theory. Melting point 266°C.

The compounds set forth in Table 3 were obtained in a manner analogous to that of Example 1 from the reactants set forth in Table IV:

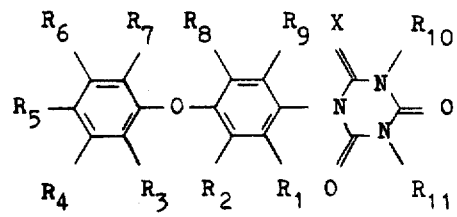

Table 3

| Example No. | R¹ | R² | R³ | R⁴ | R⁵ | R⁶ | R⁷ | R⁸ | R⁹ | R¹⁰ | R¹¹ | X | Melting point °C |
|---|---|---|---|---|---|---|---|---|---|---|---|---|---|
| 2 | H | H | H | H | NO₂ | H | H | H | H | H | H | O | 295 |
| 3 | H | Cl | Cl | H | Cl | Cl | H | H | H | H | H | O | 321 |
| 4 | H | H | H | H | CH₃ | H | H | H | H | CH₃ | H | O | 198 – 199 |
| 5 | H | H | H | H | NO₂ | H | H | H | H | CH₃ | H | O | 266 |
| 6 | H | H | NO₂ | H | H | H | H | H | H | CH₃ | H | O | 243 |

Table 3-continued

| Example No. | $R^1$ | $R^2$ | $R^3$ | $R^4$ | $R^5$ | $R^6$ | $R^7$ | $R^8$ | $R^9$ | $R^{10}$ | $R^{11}$ | X | Melting point °C |
|---|---|---|---|---|---|---|---|---|---|---|---|---|---|
| 7 | H | H | H | H | NH₂ | H | H | H | H | CH₃ | H | O | 300 |
| 8 | H | H | NH₂ | H | H | H | H | H | H | CH₃ | H | O | 294 |
| 9 | H | H | H | H | CH₃.CO.NH | H | H | H | H | CH₃ | H | O | 307 |
| 10 | H | H | H | H | Cl | H | H | H | H | CH₃ | H | O | 208 |
| 11 | H | Cl | H | H | H | H | H | H | H | CH₃ | H | O | 166 |
| 12 | H | H | H | Cl | H | H | H | H | H | CH₃ | H | O | 200 – 201 |
| 13 | H | H | H | H | COOH | H | H | H | H | CH₃ | H | O | 300 |
| 14 | H | H | H | H | COOC₂H₅ | H | H | H | H | CH₃ | H | O | 238 – 240 |
| 15 | H | H | H | H | CN | H | H | H | H | CH₃ | H | O | 245 |
| 16 | H | H | H | H | CF₃ | H | H | H | H | CH₃ | H | O | 210 |
| 17 | H | H | H | H | CH₃CO | H | H | H | H | CH₃ | H | O | 211 |
| 18 | H | H | H | H | NH.COOC₂H₅ | H | H | H | H | CH₃ | H | O | 191 – 192 |
| 19 | H | H | H | H | SO₂C₂H₅ | H | H | H | H | CH₃ | H | O | 120 (decomposition) |
| 20 | H | H | NO₂ | H | NO₂ | H | H | H | H | CH₃ | H | O | 303 |
| 21 | H | H | CN | H | CN | H | H | H | H | CH₃ | H | O | 320 |
| 22 | H | H | Cl | H | Cl | H | H | H | H | CH₃ | H | O | 208 |
| 23 | H | Cl | H | H | Cl | H | H | H | H | CH₃ | H | O | 276 |
| 24 | H | H | Cl | H | H | H | Cl | H | H | CH₃ | H | O | 275 |
| 25 | H | H | Cl | H | Cl | Cl | H | H | H | CH₃ | H | O | 261 |
| 26 | H | Cl | Cl | H | Cl | H | H | H | H | CH₃ | H | O | 232 |
| 27 | H | Cl | Cl | H | Cl | Cl | H | H | H | CH₃ | H | O | 240 |
| 28 | H | H | H | Cl | CN | H | H | H | H | CH₃ | H | O | 248 |
| 29 | H | H | CN | H | Cl | H | H | H | H | CH₃ | H | O | 260 |
| 30 | H | H | Cl | H | CN | H | H | H | H | CH₃ | H | O | 273 |
| 31 | H | Cl | H | H | CF₃ | H | H | H | H | CH₃ | H | O | 218 |
| 32 | H | H | NO₂ | H | Cl | H | H | H | H | CH₃ | H | O | 244 – 245 |
| 33 | H | H | Cl | H | H | H | NO₂ | H | H | CH₃ | H | O | 252 |
| 34 | H | H | Cl | H | NO₂ | H | H | H | CH₃ | CH₃ | H | O | 222 |
| 35 | H | H | H | Cl | NO₂ | H | H | H | H | CH₃ | H | O | 232 |
| 36 | H | Cl | Cl | H | NO₂ | H | H | H | H | CH₃ | H | O | 260 |
| 37 | Cl | H | Cl | H | NO₂ | H | H | H | H | CH₃ | H | O | 264 |
| 38 | H | H | Cl | H | NO₂ | Cl | H | H | H | CH₃ | H | O | 250 |
| 39 | Cl | H | H | Cl | NO₂ | H | H | H | H | CH₃ | H | O | 267 |
| 40 | H | H | CN | H | H | NO₂ | H | H | H | CH₃ | H | O | 312 |
| 41 | H | H | H | H | NO₂ | H | H | H | H | CH₃ | H | O | 270 |
| 42 | CH₃ | H | CH₃ | H | NO₂ | H | H | H | H | CH₃ | H | O | 212 |
| 43 | H | Cl | CH₃ | H | CH₃ | H | H | H | H | CH₃ | H | O | 196 |
| 44 | H | H | H | CH₃ | Cl | CH₃ | H | H | H | CH₃ | H | O | 240 – 241 |
| 45 | H | Cl | Cl | H | COOH | H | H | H | H | CH₃ | H | O | 174 (decomposition) |
| 46 | Cl | H | Cl | H | NH₂ | H | H | H | H | CH₃ | H | O | 269 |
| 47 | H | Cl | Cl | H | NO₂ | H | H | Cl | H | CH₃ | H | O | 316 |
| 48 | H | H | CH₃ | H | CH₃ | H | H | H | H | C₂H₅ | H | O | 198 – 199 |
| 49 | H | H | H | CH₃ | CH₃ | H | H | H | H | C₂H₅ | H | O | 193 |
| 50 | CH₃ | H | H | H | NO₂ | H | H | H | H | C₂H₅ | H | O | 229 |
| 51 | Cl | H | H | H | NO₂ | H | H | H | H | C₂H₅ | H | O | 276 |
| 52 | CH₃ | H | Cl | H | NO₂ | H | H | H | H | C₂H₅ | H | O | 240 |
| 53 | Cl | H | H | H | NH₂ | H | H | H | H | C₂H₅ | H | O | 225 |
| 54 | H | H | H | H | NO₂ | H | H | Cl | H | C₂H₅ | H | O | 198 – 200 |
| 55 | H | Cl | Cl | H | NO₂ | H | H | H | H | C₂H₅ | H | O | 152 |
| 56 | H | H | H | H | NO₂ | H | H | H | H | n–C₃H₇ | H | O | 195 – 196 |
| 57 | H | Cl | Cl | H | NO₂ | H | H | Cl | H | n–C₃H₇ | H | O | 140 |
| 58 | H | H | H | H | NO₂ | H | H | H | H | i–C₃H₇ | H | O | 202 – 203 |
| 59 | H | Cl | Cl | H | NO₂ | H | H | Cl | H | i–C₃H₇ | H | O | 155 – 157 |
| 60 | H | H | H | H | NO₂ | H | H | H | H | n–C₄H₉ | H | O | 194 – 195 |
| 61 | H | Cl | Cl | H | NO₂ | H | H | Cl | H | n–C₄H₉ | H | O | 142 – 144 |
| 62 | H | H | Cl | H | NO₂ | H | H | H | H | n–C₄H₉ | H | O | 165 |
| 63 | H | H | H | H | NO₂ | H | H | H | H | –CH=CH–CH₃ | H | O | 199 – 200 |
| 64 | H | Cl | Cl | H | NO₂ | H | H | Cl | H | –CH=CH–CH₃ | H | O | 163 |
| 65 | H | H | H | H | NO₂ | H | H | H | H | C(CH₃)₃ | H | O | 292 |
| 66 | H | H | H | H | NO₂ | H | H | H | H | C₁₀H₂₁ | H | O | 191 – 193 |
| 67 | H | H | H | H | NO₂ | H | H | H | H | CH₂CH₂Cl | H | O | 252 – 254 |
| 68 | H | H | H | H | NO₂ | H | H | H | H | C₆H₁₁ | H | O | 226 – 228 |
| 69 | H | H | H | H | NO₂ | H | H | H | H | C₆H₅ | H | O | 224 – 226 |
| 70 | H | H | H | H | NO₂ | H | H | H | H | p–Cl–C₆–H₄ | H | O | 198 – 199 |
| 71 | H | H | H | H | NO₂ | H | H | H | H | COOCH₃ | H | O | 249 |
| 72 | H | Cl | Cl | H | Cl | H | H | H | H | COOCH₃ | H | O | 212 |
| 73 | H | H | H | H | NO₂ | H | H | H | H | COOC₂H₅ | H | O | 178 – 180 |
| 74 | H | H | H | H | NO₂ | H | H | H | H | COSC₄H₉ | H | O | 193 – 194 |
| 75 | H | H | H | H | NO₂ | H | H | H | H | N(CH₃)₂ | H | O | 182 – 184 |
| 76 | H | H | H | H | NO₂ | H | H | H | H |  | H | O | 211 – 213 |
| 77 | H | H | H | H | NO₂ | H | H | H | H |  | H | O | 275 – 276 |
| 78 | H | H | H | H | NO₂ | H | H | H | H | OCH₃ | H | O | 231 |
| 79 | H | Cl | H | Cl | Cl | H | Cl | H | H | 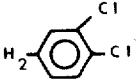 | H | O | 198 |

Table 3-continued

| Example No. | R¹ | R² | R³ | R⁴ | R⁵ | R⁶ | R⁷ | R⁸ | R⁹ | R¹⁰ | R¹¹ | X | Melting point °C |
|---|---|---|---|---|---|---|---|---|---|---|---|---|---|
| 80 | H | H | H | H | Cl | H | H | H | H | CH=CH—CH₃ | H | O | 151–152 |
| 81 | H | H | H | H | Cl | H | H | H | H | CH₂CH₂CH₂OCH₃ | H | O | 167–169 |
| 82 | H | H | H | H | Cl | H | H | H | H |  | H | O | 248–249 |
| 83 | H | H | H | H | H | H | H | H | H | CH₃ | H | S | 222 |
| 84 | H | H | H | H | NO₂ | H | H | H | H | CH₃ | H | S | 271 |
| 85 | H | Cl | H | H | H | H | H | H | H | CH₃ | H | S | 213 |
| 86 | H | H | H | H | Cl | H | H | H | H | CH₃ | H | S | 214 |
| 87 | H | Cl | H | H | Cl | H | H | H | H | CH₃ | H | S | 215 |
| 88 | H | H | Cl | H | Cl | H | H | H | H | CH₃ | H | S | 208 |
| 89 | H | Cl | Cl | H | Cl | H | H | H | H | CH₃ | H | S | 210 |
| 90 | H | Cl | Cl | H | Cl | Cl | H | H | H | CH₃ | H | S | 216 |
| 91 | H | Cl | H | H | NO₂ | H | H | Cl | H | CH₃ | H | O | 298 |
| 92 | H | Cl | H | H | Cl | H | H | Cl | H | CH₃ | H | O | 96 |
| 93 | H | Cl | H | H | Cl | H | H | Cl | H | nC₃H₇ | H | O | 105 |
| 94 | H | Cl | Cl | H | Cl | H | H | Cl | H | CH₃ | H | O | 229 |
| 95 | H | Cl | Cl | H | Cl | H | H | Cl | H | nC₃H₇ | H | O | 78 |
| 96 | H | CH₃ | H | H | Cl | H | H | CH₃ | H | CH₃ | H | O | 56 |
| 97 | H | CH₃ | H | H | Cl | H | H | CH₃ | H | nC₃H₇ | H | O | 169 |
| 98 | H | Cl | H | H | NO₂ | H | H | Cl | H | nC₃H₇ | H | O | 172 |
| 99 | H | CH₃ | H | H | NO₂ | H | H | CH₃ | H | CH₃ | H | O | 259 |
| 100 | H | CH₃ | H | H | NO₂ | H | H | CH₃ | H | nC₃H₇ | H | O | 137 |
| 101 | H | CH₃ | Cl | H | NO₂ | H | H | CH₃ | H | CH₃ | H | O | 268 |
| 102 | H | CH₃ | Cl | H | NO₂ | H | H | CH₃ | H | nC₃H₇ | H | O | 222 |
| 103 | H | Cl | H | H | CN | H | H | Cl | H | CH₃ | H | O | 132 |
| 104 | H | Cl | H | H | CN | H | H | Cl | H | nC₃H₇ | H | O | 147 |
| 105 | H | H | H | H | H₂N—CO— | H | H | Cl | H | CH₃ | H | O | 263 |
| 106 | H | Cl | Cl | H | NO₂ | H | H | Cl | H | CH₃ | H | S | >270 |
| 107 | H | Cl | Cl | H | NO₂ | H | H | Cl | H | nC₃H₇ | H | S | 245 |
| 108 | H | CH₃ | H | H | Cl | H | H | H | H | CH₃ | H | O | 237 |
| 109 | H | CH₃ | Cl | H | Cl | H | H | H | H | CH₃ | H | O | 228 |
| 110 | H | Cl | CH₃ | H | Cl | H | H | H | H | CH₃ | H | O | 219 |
| 111 | H | Cl | H | H | Cl | H | H | CH₃ | H | CH₃ | H | O | 238 |
| 112 | H | Cl | H | H | CN | H | H | Cl | H | CH₂—CH=CH₂ | H | O | 140 |
| 113 | H | H | CH₃ | H | NO₂ | H | Cl | H | H | CH₃ | H | O | 302 |
| 114 | H | CH₃ | H | H | Cl | H | Cl | Cl | H | CH₃ | H | O | 206 |
| 115 | H | CH₃ | H | H | Cl | H | Cl | Cl | H | C₂H₅ | H | O | 186 |
| 116 | H | CH₃ | H | H | Cl | H | Cl | Cl | H | C₂H₅ | H | O | 229 |
| 117 | H | CH₃ | H | H | Cl | H | Cl | Cl | H | C₂H₅ | H | O | 207 |
| 118 | H | H | CH₃ | H | NO₂ | H | Cl | H | Cl | C₂H₅ | H | O | 217 |
| 119 | H | H | H | H | Cl | H | Cl | H | H | C₂H₅ | H | O | 210 |
| 120 | H | Cl | H | Cl | H | H | Cl | H | H | C₂H₅ | H | O | 185 |
| 121 | H | H | H | Cl | CF₃ | H | Cl | H | H | C₂H₅ | H | O | 293 |
| 122 | H | H | H | Cl | CN | H | H | H | H | C₂H₅ | H | O | 232 |
| 123 | H | H | NO₂ | H | CF₃ | H | H | H | H | C₂H₅ | H | O | 228 |
| 124 | H | Cl | H | H | CN | H | H | Cl | H | C₂H₅ | H | O | 184 |
| 125 | H | H | H | H | NO₂ | H | H | H | H | n—C₃H₇ | H | S | 227 |
| 126 | H | H | CH₃ | H | NO₂ | H | CH₃ | H | H | CH₃ | H | O | >280 |
| 127 | H | H | H | H | NO₂ | H | Cl | H | H | CH₃ | H | O | >280 |
| 128 | Cl | H | Cl | H | NO₂ | H | Cl | H | H | CH₃ | H | O | 259 |
| 129 | H | Cl | H | Cl | Cl | H | H | H | H | CH₃ | H | O | 236 |
| 130 | H | Cl | H | CN | CN | H | H | H | H | n—C₃H₇ | H | O | 179 |
| 131 | H | Cl | H | H | CN | H | Cl | H | H | C₂H₅ | H | O | 218 |
| 132 | H | H | H | CF₂ | NO₂ | H | H | H | H | C₂H₅ | H | O | 221 |
| 133 | H | H | CF₃ | H | NO₂ | H | H | H | H | n—C₃H₇ | H | O | 174 |
| 134 | H | H | H | CF₃ | H | H | H | H | H | C₃H₇ | H | O | 157 |
| 135 | H | Cl | H | Cl | CN | H | H | H | H | C₂H₅ | H | O | 179 |
| 136 | H | H | CF₃ | H | H | H | H | H | H | C₂H₅ | H | O | 138 |
| 137 | H | H | Cl | H | Cl | H | CF₃ | H | H | C₂H₅ | H | O | 210 |
| 138 | H | Cl | H | H | NO₂ | H | CF₃ | H | H | C₂H₅ | H | O | 120 |
| 139 | H | CF₃ | H | H | Cl | H | Cl | Cl | H | C(CH₃)₃ | H | O | 210 |
| 140 | H | Cl | H | CF₃ | H | H | H | H | H | C₃H₇ | H | O | 151 |

Table 4

| Ex. No. | R¹ | R² | R³ | R⁴ | R⁵ | Reactants R⁶ | R⁷ | R⁸ | R⁹ | R¹⁰ | R¹¹ | X | R¹² |
|---|---|---|---|---|---|---|---|---|---|---|---|---|---|
| 2 | H | H | H | H | NO₂ | H | H | H | H | H | H | O | |
| 3 | H | Cl | Cl | H | Cl | Cl | H | H | H | H | H | O | |
| 4 | H | H | H | H | CH₃ | H | H | H | H | CH₃ | H | O | |
| 5 | H | H | H | H | NO₂ | H | H | H | H | CH₃ | H | O | |
| 6 | H | H | NO₂ | H | H | H | H | H | H | CH₃ | H | O | |
| 7 | H | H | H | NH₂ | H | H | H | H | H | CH₃ | H | O | |
| 8 | H | H | NH₂ | H | H | H | H | H | H | CH₃ | H | O | |
| 9 | H | H | H | H | CH₃.CO.NH | H | H | H | H | CH₃ | H | O | |
| 10 | H | H | H | H | Cl | H | H | H | H | CH₃ | H | O | |
| 11 | H | Cl | H | H | H | H | H | H | H | CH₃ | H | O | |
| 12 | H | H | H | H | Cl | H | H | H | H | CH₃ | H | O | |
| 13 | H | H | H | H | COOH | H | H | H | H | CH₃ | H | O | |
| 14 | H | H | H | H | COOC₂H₅ | H | H | H | H | CH₃ | H | O | |
| 15 | H | H | H | H | CN | H | H | H | H | CH₃ | H | O | |
| 16 | H | H | H | H | CF₃ | H | H | H | H | CH₃ | H | O | |

Table 4-continued

| Ex. No. | R¹ | R² | R³ | R⁴ | R⁵ | R⁶ | R⁷ | R⁸ | R⁹ | R¹⁰ | R¹¹ | X | R¹² |
|---|---|---|---|---|---|---|---|---|---|---|---|---|---|
| 17 | H | H | H | H | CH₃CO | H | H | H | H | CH₃ | H | O | |
| 18 | H | H | H | H | NH.COOC₂H₅ | H | H | H | H | CH₃ | H | O | |
| 19 | H | H | H | H | SO₂C₂H₅ | H | H | H | H | CH₃ | H | O | |
| 20 | H | H | NO₂ | H | NO₂ | H | H | H | H | CH₃ | H | O | |
| 21 | H | H | CN | H | CN | H | H | H | H | CH₃ | H | O | |
| 22 | H | H | Cl | H | Cl | H | H | H | H | CH₃ | H | O | |
| 23 | H | Cl | H | H | Cl | H | H | H | H | CH₃ | H | O | |
| 24 | H | H | Cl | H | H | H | Cl | H | H | CH₃ | H | O | |
| 25 | H | H | Cl | H | Cl | Cl | H | H | H | CH₃ | H | O | |
| 26 | H | Cl | Cl | H | Cl | H | H | H | H | CH₃ | H | O | |
| 27 | H | Cl | Cl | H | Cl | Cl | H | H | H | CH₃ | H | O | |
| 28 | H | H | H | Cl | CN | H | H | H | H | CH₃ | H | O | |
| 29 | H | H | CN | H | Cl | H | H | H | H | CH₃ | H | O | |
| 30 | H | H | Cl | H | CN | H | H | H | H | CH₃ | H | O | |
| 31 | H | H | Cl | H | CF₃ | H | H | H | H | CH₃ | H | O | |
| 32 | H | H | NO₂ | H | Cl | H | H | H | H | CH₃ | H | O | |
| 33 | H | H | Cl | H | H | H | NO₂ | H | H | CH₃ | H | O | |
| 34 | H | H | Cl | H | NO₂ | H | H | H | CH₃ | CH₃ | H | O | |
| 35 | H | H | H | Cl | NO₂ | H | H | H | H | CH₃ | H | O | |
| 36 | H | Cl | Cl | H | NO₂ | H | H | H | H | CH₃ | H | O | |
| 37 | Cl | H | Cl | H | NO₂ | H | H | H | H | CH₃ | H | O | |
| 38 | H | H | Cl | H | NO₂ | Cl | H | H | H | CH₃ | H | O | |
| 39 | Cl | H | H | Cl | NO₂ | H | H | H | H | CH₃ | H | O | |
| 40 | H | H | CN | H | H | NO₂ | H | H | H | CH₃ | H | O | |
| 41 | H | H | CH₃ | H | NO₂ | H | H | H | H | CH₃ | H | O | |
| 42 | CH₃ | H | H | H | NO₂ | H | H | H | H | CH₃ | H | O | |
| 43 | H | Cl | CH₃ | H | CH₃ | H | H | H | H | CH₃ | H | O | |
| 44 | H | H | H | CH₃ | Cl | CH₃ | H | H | H | CH₃ | H | O | |
| 45 | H | Cl | Cl | H | COOH | H | H | H | H | CH₃ | H | O | |
| 46 | Cl | H | Cl | H | NH₂ | H | H | H | H | CH₃ | H | O | |
| 47 | H | Cl | Cl | H | NO₂ | H | H | Cl | H | CH₃ | H | O | |
| 48 | H | H | CH₃ | H | CH₃ | H | H | H | H | C₂H₅ | H | O | |
| 49 | H | H | H | CH₃ | CH₃ | H | H | H | H | C₂H₅ | H | O | |
| 50 | CH₃ | H | H | H | NO₂ | H | H | H | H | C₂H₅ | H | O | |
| 51 | Cl | H | H | H | NO₂ | H | H | H | H | C₂H₅ | H | O | |
| 52 | CH₃ | H | Cl | H | NO₂ | H | H | H | H | C₂H₅ | H | O | |
| 53 | Cl | H | H | H | NH₂ | H | H | H | H | C₂H₅ | H | O | |
| 54 | H | H | H | H | NO₂ | H | H | H | H | C₂H₅ | H | O | |
| 55 | H | Cl | Cl | H | NO₂ | H | H | Cl | H | C₂H₅ | H | O | |
| 56 | H | H | H | H | NO₂ | H | H | H | H | n-C₃H₇ | H | O | |
| 57 | H | Cl | Cl | H | NO₂ | H | H | Cl | H | n-C₃H₇ | H | O | |
| 58 | H | H | H | H | NO₂ | H | H | H | H | i-C₃H₇ | H | O | |
| 59 | H | Cl | Cl | H | NO₂ | H | H | Cl | H | i-C₃H₇ | H | O | |
| 60 | H | H | H | H | NO₂ | H | H | H | H | n-C₄H₉ | H | O | |
| 61 | H | Cl | Cl | H | NO₂ | H | H | Cl | H | n-C₄H₉ | H | O | |
| 62 | H | H | Cl | H | NO₂ | H | H | H | H | n-C₄H₉ | H | O | |
| 63 | H | H | H | H | NO₂ | H | H | H | H | —CH=CH—CH₃ | H | O | |
| 64 | H | Cl | Cl | H | NO₂ | H | H | Cl | H | —CH=CH—CH₃ | H | O | |
| 65 | H | H | H | H | NO₂ | H | H | H | H | C(CH₃)₃ | H | O | |
| 66 | H | H | H | H | NO₂ | H | H | H | H | C₁₀H₂₁ | H | O | |
| 67 | H | H | H | H | NO₂ | H | H | H | H | CH₂CH₂Cl | H | O | |
| 68 | H | H | H | H | NO₂ | H | H | H | H | C₆H₁₁ | H | O | |
| 69 | H | H | H | H | NO₂ | H | H | H | H | C₆H₅ | H | O | |
| 70 | H | H | H | H | NO₂ | H | H | H | H | p-Cl—C₆—H₄ | H | O | |
| 71 | H | H | H | H | NO₂ | H | H | H | H | COOCH₃ | H | O | |
| 72 | H | Cl | Cl | H | Cl | H | H | H | H | COOCH₃ | H | O | |
| 73 | H | H | H | H | NO₂ | H | H | H | H | COOC₂H₅ | H | O | |
| 74 | H | H | H | H | NO₂ | H | H | H | H | COSC₄H₉ | H | O | |
| 75 | H | H | H | H | NO₂ | H | H | H | H | N(CH₃)₂ | H | O | |
| 76 | H | H | H | H | NO₂ | H | H | H | H | —N(piperidine) | H | O | |
| 77 | H | H | H | H | NO₂ | H | H | H | H | —N(morpholine) | H | O | |
| 78 | H | H | H | H | NO₂ | H | H | H | H | OCH₃ | H | O | |
| 79 | H | Cl | H | Cl | Cl | H | Cl | H | H | CH₂-(2,3-diClC₆H₃) | H | O | |
| 80 | H | H | H | H | Cl | H | H | H | H | CH=CH—CH₃ | H | O | |
| 81 | H | H | H | H | Cl | H | H | H | H | CH₂CH₂CH₂OCH₃ | H | O | |
| 82 | H | H | H | H | Cl | H | H | H | H | —N(morpholine) | H | O | |
| 83 | H | H | H | H | H | H | H | H | H | CH₃ | H | S | |
| 84 | H | H | H | H | NO₂ | H | H | H | H | CH₃ | H | S | |
| 85 | H | Cl | H | H | H | H | H | H | H | CH₃ | H | S | |
| 86 | H | H | H | H | Cl | H | H | H | H | CH₃ | H | S | |
| 87 | H | Cl | H | H | Cl | H | H | H | H | CH₃ | H | S | |
| 88 | H | H | Cl | H | Cl | H | H | H | H | CH₃ | H | S | |

Table 4-continued

| Ex. No. | R¹ | R² | R³ | R⁴ | R⁵ | R⁶ | R⁷ | R⁸ | R⁹ | R¹⁰ | R¹¹ | X | R¹² |
|---|---|---|---|---|---|---|---|---|---|---|---|---|---|
| 89 | H | Cl | Cl | H | Cl | H | H | H | H | CH₃ | H | S | |
| 90 | H | Cl | Cl | H | Cl | Cl | H | H | H | CH₃ | H | S | |
| 91 | H | Cl | H | H | NO₂ | H | H | Cl | H | CH₃ | H | O | |
| 92 | H | Cl | H | H | Cl | H | H | Cl | H | CH₃ | H | O | |
| 93 | H | Cl | H | H | Cl | H | H | Cl | H | nC₃H₇ | H | O | |
| 94 | H | Cl | Cl | H | Cl | H | H | Cl | H | CH₃ | H | O | |
| 95 | H | Cl | Cl | H | Cl | H | H | Cl | H | nC₃H₇ | H | O | |
| 96 | H | CH₃ | H | H | Cl | H | H | CH₃ | H | CH₃ | H | O | |
| 97 | H | CH₃ | H | H | Cl | H | H | CH₃ | H | nC₃H₇ | H | O | |
| 98 | H | Cl | H | H | NO₂ | H | H | Cl | H | nC₃H₇ | H | O | |
| 99 | H | CH₃ | H | H | NO₂ | H | H | CH₃ | H | CH₃ | H | O | |
| 100 | H | CH₃ | H | H | NO₂ | H | H | CH₃ | H | nC₃H₇ | H | O | |
| 101 | H | CH₃ | Cl | H | NO₂ | H | H | CH₃ | H | CH₃ | H | O | |
| 102 | H | CH₃ | Cl | H | NO₂ | H | H | CH₃ | H | nC₃H₇ | H | O | |
| 103 | H | Cl | H | H | CN | H | H | Cl | H | CH₃ | H | O | |
| 104 | H | Cl | H | H | CN | H | H | Cl | H | nC₃H₇ | H | O | |
| 105 | H | H | H | H | H₂N—CO— | H | H | H | H | CH₃ | H | O | |
| 106 | H | Cl | Cl | H | NO₂ | H | H | Cl | H | CH₃ | H | S | |
| 107 | H | Cl | Cl | H | NO₂ | H | H | Cl | H | nC₃H₇ | H | S | |
| 108 | H | CH₃ | H | H | Cl | H | H | H | H | CH₃ | H | O | |
| 109 | H | CH₃ | Cl | H | Cl | H | H | H | H | CH₃ | H | O | |
| 110 | H | Cl | CH₃ | H | Cl | H | H | H | H | CH₃ | H | O | |
| 111 | H | Cl | H | H | Cl | H | H | CH₃ | H | CH₃ | H | O | |
| 112 | H | Cl | H | H | CN | H | H | Cl | H | CH₂—CH=CH₂ | H | O | |
| 113 | H | H | CH₃ | H | NO₂ | H | Cl | H | H | CH₃ | H | O | |
| 114 | H | CH₃ | H | H | Cl | H | Cl | Cl | H | CH₃ | H | O | |
| 115 | H | CH₃ | H | Cl | Cl | H | Cl | Cl | H | C₂H₅ | H | O | |
| 116 | H | CH₃ | H | H | Cl | H | Cl | Cl | H | C₂H₅ | H | O | |
| 117 | H | CH₃ | H | Cl | Cl | H | Cl | Cl | H | C₂H₅ | H | O | |
| 118 | H | H | CH₃ | H | NO₂ | H | H | Cl | Cl | C₂H₅ | H | O | |
| 119 | H | H | H | Cl | Cl | H | H | H | H | C₂H₅ | H | O | |
| 120 | H | Cl | H | Cl | H | H | Cl | H | H | C₂H₅ | H | O | |
| 121 | H | H | H | Cl | CF₃ | H | Cl | H | H | C₂H₅ | H | O | |
| 122 | H | H | H | Cl | CN | H | H | H | H | C₂H₅ | H | O | |
| 123 | H | H | NO₂ | H | CF₃ | H | H | H | H | C₂H₅ | H | O | |
| 124 | H | Cl | H | H | CN | H | H | Cl | H | C₂H₅ | H | O | |
| 125 | H | H | H | H | NO₂ | H | H | H | H | n-C₃H₇ | H | S | |
| 126 | H | H | CH₃ | H | NO₂ | H | CH₃ | H | H | CH₃ | H | O | |
| 127 | H | H | Cl | H | NO₂ | H | Cl | H | H | CH₃ | H | O | |
| 128 | Cl | H | Cl | H | NO₂ | H | Cl | H | H | CH₃ | H | O | |
| 129 | H | Cl | H | Cl | Cl | H | H | H | H | CH₃ | H | O | |
| 130 | H | Cl | H | CN | CN | H | H | H | H | n-C₃H₇ | H | O | |
| 131 | H | Cl | H | H | CN | H | Cl | H | H | C₂H₅ | H | O | |
| 132 | H | H | H | CF₃ | NO₂ | H | H | H | H | C₂H₅ | H | O | |
| 133 | H | H | CF₃ | H | NO₂ | H | H | H | H | n-C₃H₇ | H | O | |
| 134 | H | H | H | H | CF₃ | H | H | H | H | C₃H₇ | H | O | |
| 135 | H | Cl | H | Cl | CN | H | H | H | H | C₂H₅ | H | O | |
| 136 | H | H | H | H | CF₃ | H | H | H | H | C₂H₅ | H | O | |
| 137 | H | H | Cl | H | Cl | H | CF₃ | H | H | C₂H₅ | H | O | |
| 138 | H | Cl | H | H | NO₂ | H | CF₃ | H | H | C₂H₅ | H | O | |
| 139 | H | CF₃ | H | H | Cl | H | Cl | Cl | H | C(CH₃)₃ | H | O | |
| 140 | H | Cl | H | CF₃ | H | H | H | H | H | C₃H₇ | H | O | |

EXAMPLE 141

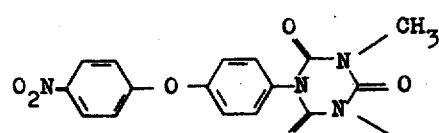

3.2 g (0.025 mol) of dimethyl sulphate are added dropwise, at room temperature, to a solution of 8.9 g (0.025 mol) of 1-[4-(4'-nitro-phenoxy)-phenyl]-3-methyl-1,3,5-triazine-2,4,6(1H,3H,5H)-trione and 1.6 g (0.028 mol) of potassium hydroxide in 200 ml of water. Thereafter the mixture is heated to 90°C for 1 hour.

After cooling, 1-[4-(4'-nitro-phenoxy)-phenyl]-3,5-dimethyl-1,3,5-triazine-2,4,6(1H,3H,5H)-trione precipitates as crystals. It is filtered off and boiled with ethanol.

Yield 75% of theory. Melting point 199° - 200°C.

EXAMPLE 142

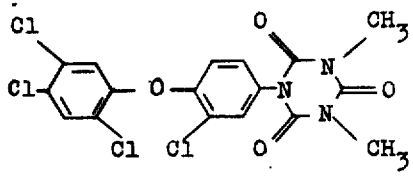

The dry residue from a reaction of an 0.1 molar sodium ethylate solution with 45 g (0.1 mol) of 1-[3-chloro-4-4',5'-trichloro-phenoxy)-phenyl]-3-methyl-1,3,5-triazine-2,4,6(1H,3H,5H)-trione is dissolved in 25 ml of dimethylformamide and 14.2 g (0.1 mol) of methyl iodide — diluted with a few ml dimethyl formamide — are added dropwise at room temperature, whilst stirring. Thereafter the mixture is warmed for 2 hours at 50°C, the solvent is then stripped off in vacuo, and the residue, in toluene, is filtered hot to remove unreacted starting material and sodium iodide. The residue from evaporating the toluene filtrate contains 1-[3-chloro-4-(2',4',5'-trichloro-phenoxy)-phenyl]-3,5-dimethyl-1,3,5-triazine-2,4,6(1H,3H,5H)-trione. It can be purified by recrystallisation from methanol-ethyl acetate. Yield 64% of theory. Melting point 207° – 208°C.

What is claimed is:

1. A 1-(4-phenoxy-phenyl)-1,3,5-triazine of the formula:

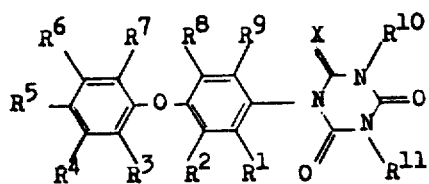

or a pharmaceutically acceptable nontoxic salt thereof wherein $R^1$, $R^2$, $R^3$, $R^4$, $R^5$, $R^6$, $R^7$, $R^8$ and $R^9$ are the same or different and are each hydrogen, straight or branched chain lower alkyl, trifluoromethyl, halogen, nitro, cyano, amino, lower alkanoylamine, lower alkoxycarbonylamine, carboxyl, lower alkoxycarbonyl, aminocarbonyl, lower alkylcarbonyl, lower alkylsulphonyl, or aminosulphonyl;

$R^{10}$ is hydrogen, straight or branched chain lower alkyl, cyclohexyl, haloalkyl of one or two carbon atoms in the alkyl moiety and one halo moiety, lower alkoxy lower alkyl, lower alkenyl, lower alkinyl, lower alkoxycarbonyl, thiolower alkylcarbonyl, lower alkoxy, dilower alkylamino, piperidyl, morpholino, benzyl unsubstituted or substituted by one or two halogen moieties, or phenyl unsubstituted or substituted by halogen;

$R^{11}$ is hydrogen or lower alkyl; and

X is oxygen or sulfur.

2. A compound according to claim 1 wherein $R^1$, $R^2$, $R^3$, $R^4$, $R^5$, $R^6$, $R^7$, $R^8$ and $R^9$ are the same or different and each are hydrogen, straight chain alkyl of one to four carbon atoms, trifluoromethyl, chlorine, bromine, nitro, cyano, amino, alkanoylamino of one to four carbon atoms in the alkyl moiety, alkoxycarbonylamino of one to four carbon atoms in the alkoxy moiety, carboxyl, alkoxycarbonyl of one to four carbon atoms in the alkoxy moiety, aminocarbonyl, alkylcarbonyl of one to four carbon atoms in the alkyl moiety, alkylsulphonyl of one to four carbon atoms in the alkyl moiety, or aminosulphonyl;

$R^{10}$ is hydrogen, straight chain alkyl of one to twelve carbon atoms, branched chain alkyl of three to five carbon atoms, an ω-chloroalkyl moiety of one to six carbon atoms, an ω-methoxyalkyl moiety of two to five carbon atoms, alkenyl of two to four carbon atoms, alkoxycarbonyl to one to four carbon atoms in the alkoxy moiety, thioalkylcarbonyl of one to four carbon atoms in the alkyl moiety, dialkylamine wherein each alkyl moiety is the same and each alkyl moiety is of one to four carbon atoms, piperidyl, morpholino, phenyl or chlorophenyl; and $R^{11}$ is hydrogen or alkyl of one to four carbon atoms.

3. A compound according to claim 1 wherein $R^1$, $R^2$, $R^3$, $R^4$, $R^5$, $R^6$, $R^7$, $R^8$ and $R^9$ are the same or different and each are hydrogen, chlorine, methyl, nitro, cyano, amino, trifluoromethyl, methylcarbonylamino, carboxyl, acetyl, carbethoxy, carbethoxyamino, ethylsulphonyl, aminocarbonyl, or aminosulphonyl;

$R^{10}$ is hydrogen, straight or branched chain alkyl of one to 10 carbon atoms, allyl, chloroethyl, alkoxycarbonyl of one or two carbon atoms in the alkoxy moiety, thioalkylcarbonyl of one to four carbon atoms in the alkyl moiety, methoxy, methoxyalkyl of one to three carbon atoms, dimethylamino, phenyl, chlorophenyl, dichlorotolyl, piperidyl or morpholino;

$R^{11}$ is hydrogen; and

X is oxygen or sulfur.

4. A compound according to claim 1 wherein $R^1$ is hydrogen, chlorine or methyl;

$R^2$ is hydrogen, chlorine, methyl, trifluoromethyl or nitro;

$R^3$ is hydrogen, chlorine, nitro, amino, cyano, methyl or trifluoromethyl;

$R^4$ is hydrogen, chlorine, methyl, cyano or trifluoromethyl;

$R^5$ is hydrogen, chlorine, methyl, nitro, amino, methylcarbonylamino, carboxyl, carbethoxy, cyano, trifluoromethyl, acetyl, carbethoxyamino, ethylsulphonyl, aminocarbonyl or aminosulphonyl;

$R^6$ is hydrogen, chlorine, methyl or nitro;

$R^7$ is hydrogen, chlorine, methyl, nitro or trifluoromethyl;

$R^8$ is hydrogen, chlorine or methyl;

$R^9$ is hydrogen, chlorine or methyl;

$R^{10}$ is hydrogen, methyl, ethyl, n-propyl, i-propyl, n-butyl, t-butyl, hexyl, decyl, chloroethyl, allyl, methoxy, methoxypropyl, methoxycarbonyl, carbethoxy, thiobutylcarbonyl, phenyl, chlorophenyl, dichlorotolyl, pyridyl, or morpholino;

$R^{11}$ is hydrogen; and

X is oxygen or sulfur.

5. The compound according to claim 1 wherein $R^1$, $R^2$, $R^3$, $R^4$, $R^6$, $R^7$, $R^8$, $R^9$ and $R^{11}$ are each hydrogen;

$R^5$ is $NO_2$;

$R^{10}$ is $CH_3$; and

X is oxygen.

6. The compound according to claim 1 wherein $R^1$, $R^2$, $R^3$, $R^4$, $R^6$, $R^7$, $R^8$, $R^9$ and $R^{11}$ are each hydrogen;

$R^5$ is Cl;

$R^{10}$ is $CH_3$; and

X is oxygen.

7. The compound according to claim 1 wherein $R^1$, $R^2$, $R^3$, $R^4$, $R^6$, $R^7$, $R^8$, $R^9$ and $R^{11}$ are each hydrogen;

$R^5$ is CN;

$R^{10}$ is $CH_3$; and

X is oxygen.

8. The compound according to claim 1 wherein $R^1$, $R^2$, $R^3$, $R^4$, $R^6$, $R^7$, $R^8$, $R^9$ and $R^{11}$ are each hydrogen;

$R^5$ is $CF_3$;

$R^{10}$ is $CH_3$; and

X is oxygen.

9. The compound according to claim 1 wherein $R^1$, $R^4$, $R^6$, $R^7$, $R^8$, $R^9$ and $R^{11}$ are each hydrogen;

$R^2$, $R^3$ and $R^5$ are Cl;

$R^{10}$ is $CH_3$; and

X is oxygen.

10. The compound according to claim 1 wherein $R^1$, $R^2$, $R^3$, $R^6$, $R^7$, $R^8$, $R^9$ and $R^{11}$ are each hydrogen;
$R^4$ is Cl;
$R^5$ is CN;
$R^{10}$ is $CH_3$; and X is oxygen.

11. The compound according to claim 1 wherein $R^1$ and $R^3$ are Cl;
$R^2$, $R^4$, $R^6$, $R^7$, $R^8$, $R^9$ and $R^{11}$ are each hydrogen;
$R^5$ is $NO_2$;
$R^{10}$ is $CH_3$; and
X is oxygen.

12. The compound according to claim 1 wherein $R^1$, $R^4$, $R^6$, $R^7$, $R^9$ and $R^{11}$ are each hydrogen;
$R^2$, $R^3$ and $R^8$ are Cl;
$R^5$ is $NO_2$;
$R^{10}$ is $CH_3$; and
X is oxygen.

13. The compound according to claim 1 wherein $R^1$ is $CH_3$;
$R^2$, $R^3$, $R^4$, $R^6$, $R^7$, $R^8$, $R^9$ and $R^{11}$ are each hydrogen;
$R^5$ is $NO_2$;
$R^{10}$ is $C_2H_5$; and
X is oxygen.

14. The compound according to claim 1 wherein $R^1$, $R^2$, $R^3$, $R^4$, $R^6$, $R^7$, $R^8$, $R^9$ and $R^{11}$ are each hydrogen;
$R^5$ is $NO_2$;
$R^{10}$ is $C_2H_5$; and
X is oxygen.

15. The compound according to claim 1 wherein $R^1$, $R^2$, $R^3$, $R^4$, $R^6$, $R^7$, $R^8$, $R^9$ and $R^{11}$ are each hydrogen;
$R^5$ is $NO_2$;
$R^{10}$ is $n-C_3H_7$; and
X is oxygen.

16. The compound according to claim 1 wherein $R^1$, $R^2$, $R^3$, $R^4$, $R^6$, $R^7$, $R^8$, $R^9$ and $R^{11}$ are each hydrogen;
$R^5$ is $NO_2$;
$R^{10}$ is $i-C_3H_7$; and
X is oxygen.

17. The compound according to claim 1 wherein $R^1$, $R^2$, $R^4$, $R^6$, $R^7$, $R^8$, $R^9$ and $R^{11}$ are each hydrogen;
$R^3$ is Cl;
$R^5$ is $NO_2$;
$R^{10}$ is $n-C_4H_9$; and
X is oxygen.

18. The compound according to claim 1 wherein $R^1$, $R^2$, $R^3$, $R^4$, $R^6$, $R^7$, $R^8$, $R^9$ and $R^{11}$ are each hydrogen;
$R^5$ is $NO_2$;
$R^{10}$ is $-CH=CH-CH_3$; and
X is oxygen.

19. The compound according to claim 1 wherein $R^1$, $R^2$, $R^3$, $R^4$, $R^6$, $R^7$, $R^8$, $R^9$ and $R^{11}$ are each hydrogen;
$R^5$ is $NO_2$;
$R^{10}$ is $CH_3$; and
X is sulfur.

20. The compound according to claim 1 wherein $R^1$, $R^2$, $R^3$, $R^4$, $R^6$, $R^7$, $R^8$, $R^9$ and $R^{11}$ are each hydrogen;
$R^5$ is Cl;
$R^{10}$ is $CH_3$; and
X is sulfur.

21. The compound according to claim 1 wherein $R^1$, $R^4$, $R^6$, $R^7$, $R^8$, $R^9$ and $R^{11}$ are each hydrogen;
$R^2$, $R^3$ and $R^5$ are Cl;
$R^{10}$ is $CH_3$; and
X is sulfur.

22. The compound according to claim 1 wherein $R^1$, $R^3$, $R^4$, $R^6$, $R^7$, $R^9$ and $R^{11}$ are each hydrogen;
$R^2$ and $R^8$ are Cl;
$R^5$ is $NO_2$;
$R^{10}$ is $CH_3$; and
X is oxygen.

* * * * *